United States Patent

Maurer et al.

[11] Patent Number: 4,695,646
[45] Date of Patent: Sep. 22, 1987

[54] AMINOACRYLIC ACID DERIVATIVES

[75] Inventors: Fritz Maurer, Wuppertal; Klaus Grohe, Odenthal, both of Fed. Rep. of Germany

[73] Assignee: Bayer Aktiengesellschaft, Leverkusen, Fed. Rep. of Germany

[21] Appl. No.: 816,544

[22] Filed: Jan. 6, 1986

[30] Foreign Application Priority Data

Jan. 16, 1985 [DE] Fed. Rep. of Germany ....... 3501247

[51] Int. Cl.$^4$ .................. C07C 101/78; C07C 69/738
[52] U.S. Cl. ......................................... 560/43; 560/53
[58] Field of Search ....................... 560/34, 53, 43, 39; 568/337

[56] References Cited

U.S. PATENT DOCUMENTS

| | | | |
|---|---|---|---|
| 3,462,536 | 8/1969 | Chemerda et al. | 560/34 |
| 3,843,710 | 10/1974 | Buckler et al. | 560/39 |
| 3,869,513 | 3/1975 | Buckman et al. | 568/337 |
| 3,950,408 | 4/1976 | Chamberlin et al. | 568/337 |
| 4,243,406 | 1/1981 | Brannigan et al. | 71/88 |
| 4,245,106 | 1/1981 | Brannigan et al. | 548/378 |

FOREIGN PATENT DOCUMENTS

| | | | |
|---|---|---|---|
| 78362 | 5/1983 | European Pat. Off. | |
| 940596 | 10/1963 | United Kingdom | 560/34 |

OTHER PUBLICATIONS

Sacchar et al, *Chemical Abstracts*, vol. 99, No. 139709a (1983).
Joshi et al, *Chemical Abstracts*, vol. 58, No. 2397h (1963).
Buu-Hoi et al, *Chemical Abstracts*, vol. 49, No. 159109c (1955).

Primary Examiner—Donald B. Moyer
Assistant Examiner—Bruce D. Gray
Attorney, Agent, or Firm—Sprung Horn Kramer & Woods

[57] ABSTRACT

Aminoacrylic and derivatives of the formula

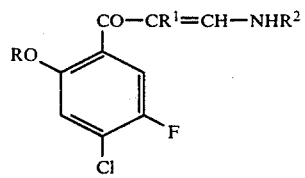

in which
R is alkyl,
$R^1$ is alkoxycarbonyl, and
$R^2$ is alkyl, cycloalkyl, amino, alkylamino or dialkylamino, and intermediates therefor. The compounds can be converted into antibacterially active known oxyquinolinecarboxylic acid derivatives.

6 Claims, No Drawings

AMINOACRYLIC ACID DERIVATIVES

The present invention relates to new aminoacrylic acid derivatives, to a process for their preparation, and to their use as an intermediate for the preparation of oxoquinolinecarboxylic acid derivatives.

It is already known that oxoquinolinecarboxylic acid derivatives can be obtained by using aminoacrylic acid derivatives as intermediates. The preparation of these aminoacrylic acid derivatives is, however, expensive and takes place in several stages (compare, for example, EP-OS (European Published Specification) No. 78,362).

The present invention relates to:

1. New aminoacrylic acid derivatives of the formula (I)

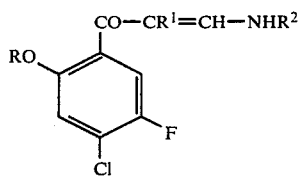

in which
R represents alkyl,
$R^1$ represents alkoxycarbonyl and
$R^2$ represents alkyl, cycloalkyl, amino, alkylamino or dialkylamino.

2. A process for the preparation of the new aminoacrylic acid derivatives of the formula (I)

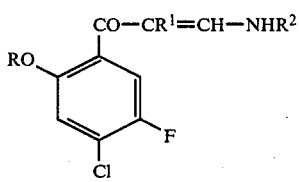

in which
R represents alkyl,
$R^1$ represents alkoxycarbonyl and
$R^2$ represents alkyl, cycloalkyl, amino, alkylamino or dialkylamino,
which is characterized in that acrylic acid derivatives of the formula (II)

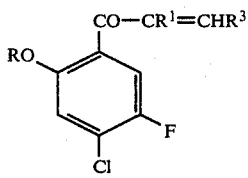

in which
R and $R^1$ have the meaning given (above) under 1 and
$R^3$ represents alkoxy,
are reacted with amines of the formula (III)

$R^2NH_2$     (III)

in which
$R^2$ has the meaning given under 1 (above), if appropriate in the presence of inert diluents.

3. Acrylic acid derivatives of the formula (II)

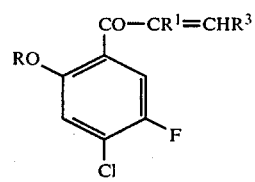

in which
R, $R^1$ and $R^3$ have the meanings given (above) under 2.

4. A process for the preparation of the new acrylic acid derivatives of the formula (II)

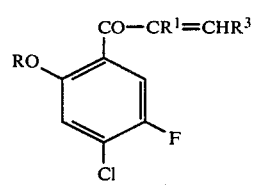

in which
R, $R^1$ and $R^3$ have the meanings given (above) under 2,
which is characterized in that 2-alkoxy-4-chloro-5-fluoro-benzoylacetates of the formula (IV)

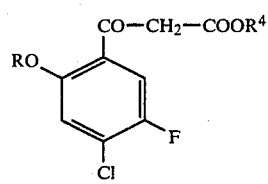

in which
R has the meaning given above and
$R^4$ represents alkyl,
are reacted with orthoformates of the formula (V)

$HC(R^3)_3$     (V)

in which
$R^3$ has the meaning given above,
in the presence of acetic anhydride and, if appropriate, in the presence of diluents.

5. 2-Alkoxy-4-chloro-5-fluoro-benzoylacetates of the formula (IV)

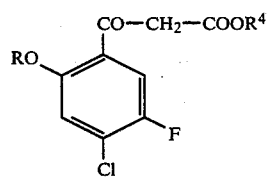

in which
R and $R^4$ have the meanings given (above) under 4.

6. A process for the preparation of the new 2-alkoxy-4-chloro-5-fluoro-benzoylacetates of the formula (IV)

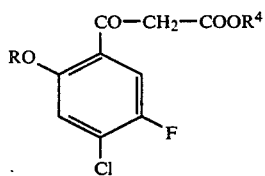 (IV)

in which
R and R⁴ have the meanings given (above) under 4, which is characterized in that acetophenones of the formula (VI)

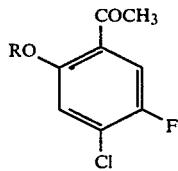 (VI)

in which
R has the meaning given (above) under 5, are reacted with dialkyl carbonates of the formula (VII)

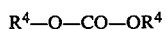 R⁴—O—CO—OR⁴ (VII)

in which
R⁴ has the meaning given (above) under 5, in the presence of strong bases 7. Acetophenones of the formula (VI)

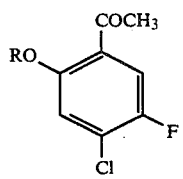 (VI)

in which
R has the meaning given (above) under 5.

8. A process for the preparation of the acetophenones of the formula (VI)

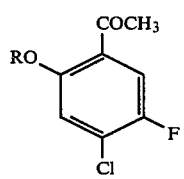 (VI)

in which
R has the meaning given (above) under 5, which is characterized in that 4-chloro-5-fluoro-2-hydroxyacetophenone of the formula (VIII)

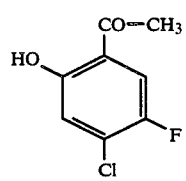 (VIII)

is reacted (∞) with allyl halides of the formula (IX)

 R—Hal (IX)

in which
R has the meaning given above and
Hal represents halogen,
or
(β) with dialkyl sulphates of the formula (X)

 RO—SO₂—OR (X)

in which
R has the meaning given above,
in the presence of acid acceptors and in the presence of diluents.

9. 4-Chloro-5-fluoro-2-hydroxyacetophenone of the formula (VIII)

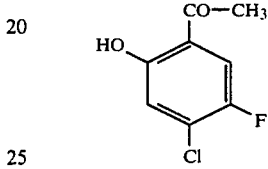 (VIII)

10. Process for the preparation of 4-chloro-5-fluoro-2-hydroxyacetophenone of the formula (VIII), characterized in that 3-chloro-4-fluorophenol of the formula (XI)

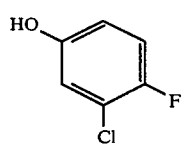 (XI)

is reacted with acetylating agents of the formula (XII)

$$CH_3\overset{O}{\overset{\|}{C}}-W$$ (XII)

in which
W represents halogen or the radical CH₃—COO—, in the presence of acylation catalysts and, if appropriate, in the presence of diluents.

11. Use of compounds of the formula (I) according to 1 (above) for the preparation of oxoquinolinecarboxylic acid derivatives, characterized in that the compounds of the formula (I) are cyclized and then converted by known methods into oxoquinolinecarboxylic acid derivatives (compare, for example, EP-OS (European Published Specification) No. 78,362).

By means of the compounds according to the invention, of the formula (I), oxoquinolinecarboxylic acid derivatives can surprisingly be prepared in a simpler and hence less expensive manner than is known from the state of the art (compare EP-OS (European Published Specification) No. 78,362). According to the state of the art, the substituted ethyl benzoylacetates are prepared by saponifying, for example, trihalogenomethylbenzene derivatives, converting the acid with thionyl chloride into the corresponding benzoyl chloride and subsequently reacting the latter with diethyl malonate in the presence of magnesium alcoholate to give a benzoylmalonic ester derivative. The ethyl benzoylacetate is then formed by partial saponification and decarboxylation in an aqueous medium with catalytic amounts of p-toluenesulphonic acid. The further conversion of the ethyl benzoylacetates initially takes place analogously to the process indicated in EP-OS (European Published Specification) No. 78,362 by reaction with O-formate and subsequent reaction with amines. This is followed by cyclization in the presence of acid acceptors and with elimination of alcohol. These compounds can then react further, by known methods, to give the corresponding oxoquinolinecarboxylic acid derivatives (compare, for example, EP-OS (European Published Specification) No. 78,362).

Preferably, the invention relates to compounds of the formula (I)
in which
R represents $C_1$–$C_4$-alkyl,
$R^1$ represents $C_1$–$C_4$-alkoxycarbonyl and
$R^2$ represents $C_1$–$C_4$-alkyl, $C_3$–$C_6$-cycloalkyl, amino $C_1$–$C_4$-alkylamino or di-$(C_1$–$C_4)$-alkylamino.

Those compounds of the formula (I) are particularly preferred
in which
R represents methyl, ethyl or n-propyl,
$R^1$ represents methoxycarbonyl, ethoxycarbonyl or n-propoxycarbonyl and
$R^2$ represents methyl, ethyl, cyclopropyl, amino, $(C_1$–$C_2)$-alkylamino or di-$(C_1$–$C_2)$-alkylamino.

If, for example, ethyl 3-ethoxy-2-(4-chloro-5-fluoro-2-ethoxy-benzoyl)-acrylate and cyclopropylamine are used as the starting substances for the process (2) according to the invention for the preparation of the compounds of the formula (I) according to the invention, the reaction can be represented by the following equation:

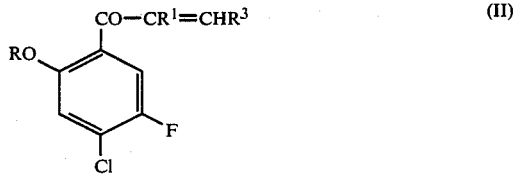

The acrylic acid derivatives to be used as starting materials for the process (2) according to the invention are generally defined by the formula (II). In this formula, R and $R^1$ preferably represent those radicals which are indicated above for the formula (I). $R^3$ in this formula represents alkoxy. Preferably, $R^3$ represents $C_1$–$C_4$-alkoxy.

The compounds of the formula (II) are new. They can be prepared according to 4 (above) (see further below).

The following may be mentioned as examples of the compounds of the formula (II):

TABLE 1

| R | $R^1$ | $R^3$ | R | $R^1$ | $R^3$ |
|---|---|---|---|---|---|
| $CH_3$ | —$COOCH_3$ | $OCH_3$ | $CH_3$ | —$COOCH_3$ | $OC_2H_5$ |
| $C_2H_5$ | —$COOCH_3$ | $OCH_3$ | $C_2H_5$ | —$COOCH_3$ | $OC_2H_5$ |
| n-$C_3H_7$ | —$COOCH_3$ | $OCH_3$ | n-$C_3H_7$ | —$COOCH_3$ | $OC_2H_5$ |
| i-$C_3H_7$ | —$COOCH_3$ | $OCH_3$ | i-$C_3H_7$ | —$COOCH_3$ | $OC_2H_5$ |
| n-$C_3H_9$ | —$COOCH_3$ | $OCH_3$ | n-$C_4H_9$ | —$COOCH_3$ | " |
| i-$C_4H_9$ | —$COOCH_3$ | $OCH_3$ | i-$C_4H_9$ | —$COOCH_3$ | " |
| sec.-$C_4H_9$ | —$COOCH_3$ | $OCH_3$ | sec.-$C_4H_9$ | —$COOCH_3$ | " |
| tert.-$C_4H_9$ | —$COOCH_3$ | $OCH_3$ | tert.-$C_4H_9$ | —$COOCH_3$ | " |
| $CH_3$ | —$COOC_2H_5$ | $OCH_3$ | $CH_3$ | —$COOC_2H_5$ | " |
| $C_2H_5$ | " | " | $C_2H_5$ | " | " |
| n-$C_3H_7$ | " | " | n-$C_3H_7$ | " | " |
| i-$C_3H_7$ | " | " | i-$C_3H_7$ | " | " |
| n-$C_4H_9$ | " | " | n-$C_4H_9$ | " | " |
| i-$C_4H_9$ | " | " | i-$C_4H_9$ | " | " |
| sec.-$C_4H_9$ | " | " | sec.-$C_4H_9$ | " | " |
| tert.-$C_4H_9$ | " | " | tert.-$C_4H_9$ | " | " |
| $CH_3$ | —$COOC_3H_7$—n | $OCH_3$ | $CH_3$ | —$COOC_3H_7$—n | " |
| $C_2H_5$ | " | " | $C_2H_5$ | " | " |
| n-$C_3H_7$ | " | " | n-$C_3H_7$ | " | " |
| i-$C_3H_7$ | " | " | i-$C_3H_7$ | " | " |
| n-$C_4H_9$ | " | " | n-$C_4H_9$ | " | " |
| i-$C_4H_9$ | " | " | i-$C_4H_9$ | " | " |
| sec.-$C_4H_9$ | " | " | sec.-$C_4H_9$ | " | " |
| tert.-$C_4H_9$ | " | " | tert.-$C_4H_9$ | " | " |
| $CH_3$ | —$COOC_3H_7$—i | $OCH_3$ | $CH_3$ | —$COOC_3H_7$—i | " |
| $C_2H_5$ | " | " | $C_2H_5$ | " | " |
| n-$C_3H_7$ | " | " | n-$C_3H_7$ | " | " |
| i-$C_3H_7$ | " | " | i-$C_3H_7$ | " | " |
| n-$C_4H_9$ | " | " | n-$C_4H_9$ | " | " |
| i-$C_4H_9$ | —$COOC_3H_7$—i | $OCH_3$ | i-$C_4H_9$ | —$COOC_3H_7$—i | $OC_2H_5$ |
| sec.-$C_4H_9$ | " | " | sec.-$C_4H_9$ | " | " |

TABLE 1-continued

| R | R¹ | R³ | R | R¹ | R³ |
|---|---|---|---|---|---|
| tert.-C₄H₉ | " | " | tert.-C₄H₉ | ", | " |
| CH₃ | —COOC₄H₉—n | " | CH₃ | —COOC₄H₉—n | " |
| C₂H₅ | " | " | C₂H₅ | " | " |
| n-C₃H₇ | " | " | n-C₃H₇ | " | " |
| i-C₃H₇ | " | " | i-C₃H₇ | " | " |
| n-C₄H₉ | " | " | n-C₄H₉ | " | " |
| i-C₄H₉ | " | " | i-C₄H₉ | " | " |
| sec.-C₄H₉ | " | " | sec.-C₄H₉ | " | " |
| tert.-C₄H₉ | " | " | tert.-C₄H₉ | " | " |
| CH₃ | —COOCH₃ | OC₃H₇—n | CH₃ | —COOC₃H₇—n | OC₃H₇—n |
|  |  |  | C₂H₅ | " | " |
| C₂H₅ | " | " | n-C₃H₇ | " | " |
|  |  |  | i-C₃H₇ | " | " |
| n-C₃H₇ | " | " | n-C₄H₉ | " | " |
| i-C₃H₇ | " | " | i-C₄H₉ | " | " |
|  |  |  | sec.-C₄H₉ | " | " |
| n-C₄H₉ | " | " | tert.-C₄H₉ | " | " |
|  |  |  | CH₃ | —COOC₃H₇—i | " |
| i-C₄H₉ | " | " | C₂H₅ | " | " |
|  |  |  | n-C₃H₇ | " | " |
| sec.-C₄H₉ | " | " | i-C₃H₇ | " | " |
|  |  |  | n-C₄H₉ | " | " |
| tert.-C₄H₉ | " | " | i-C₄H₉ | " | " |
|  |  |  | sec.-C₄H₉ | " | " |
| CH₃ | —COOC₂H₅ | OC₃H₇—n | tert.-C₄H₉ | —COOC₃—H₇—i | OC₃H₇—n |
| C₂H₅ | " | " | CH₃ | —COOC₄—H₉—n | " |
| n-C₄H₇ | " | " | C₂H₅ | " | " |
| i-C₃H₇ | " | " | n-C₃H₇ | " | " |
| n-C₄H₉ | " | " | i-C₃H₇ | " | " |
| i-C₄H₉ | " | " | n-C₄H₉ | " | " |
| sec.-C₄H₉ | " | " | i-C₄H₉ | " | " |
| tert.-C₄H₉ | " | " | sec.-C₄H₉ | " | " |
|  |  |  | tert.-C₄H₉ |  |  |

The amines which are to be used as the other starting materials for the process (2) according to the invention are generally defined by the formula (III). In this formula, $R^2$ preferably represents those radicals which are indicated above under formula (I).

The compounds of the formula (II) are novel.

The following may be mentioned as examples of compounds of the formula (III): Methylamine, ethylamine, n-propylamine, i-propylamine, n-butylamine, i-pentylamine, sec.-butylamine, tert.-butylamine, cyclopropylamine, cyclopentylamine and cyclohexylamine; hydrazine, methylhydrazine, 1,1-dimethylhydrazine, ethylhydrazine and 1,1-diethylhydrazine.

The process (2) according to the invention for the preparation of the new compounds of the formula (I) is preferably carried out with the use of diluents. Virtually any inert organic solvents can be used as the diluents.

These include, in particular, aliphatic and aromatic, optionally halogenated hydrocarbons, such as pentane, hexane, heptane, cyclohexane, petroleum ether, naphtha, ligroin, benzene, toluene, xylene, methylene chloride, ethylene chloride, chloroform, carbon tetrachloride, chlorobenzene, o-dichlorobenzene, ethers such as diethyl ether, dibutyl ether, glycol dimethyl ether and diglycol dimethyl ether, tetrahydrofuran and dioxane, and alcohols such as methanol, ethanol, isopropanol and glycol.

The process (2) according to the invention is generally carried out at temperatures between $-20°$ C. and $+50°$ C. The range between $-10°$ C. and $30°$ C. is preferred. The reactions are in general carried out under normal pressure.

For carrying out the process (2) according to the invention, the starting materials are usually employed in approximately equimolar quantities. An excess of one or the other reaction component does not have any significant advantages. Working-up is by customary methods.

If, for example, methyl 4-chloro-5-fluoro-2-methoxy-benzoylacetate and triethyl orthoformate are used as the starting materials for the process (4) according to the invention for the preparation of the compounds of the formula (II) according to the invention, the reaction can be represented by the following equation:

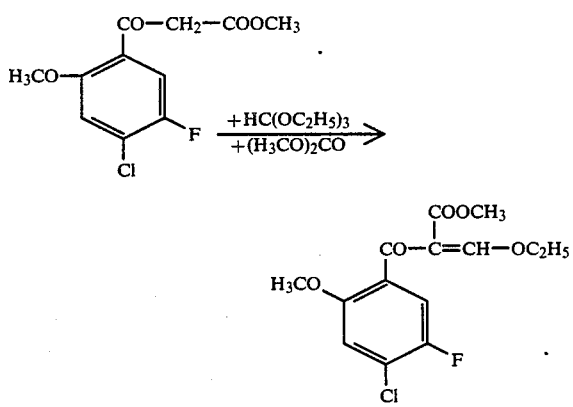

The 2-alkoxy-4-chloro-5-fluoro-benzoylacetates to be used as the starting materials for the process (4) according to the invention are generally defined by the formula (IV). In this formula R preferably represents those radicals which are indicated above for formula (I).

In this formula, $R^4$ represents alkyl. Preferably, $R^4$ represents $C_1$-$C_4$-alkyl, and particularly preferably represents methyl, ethyl, isopropyl or butyl.

The compounds of the formula (IV) are new. They can be prepared according to 6 (above) (see further below).

The following may be mentioned as examples of compounds of the formula (IV):

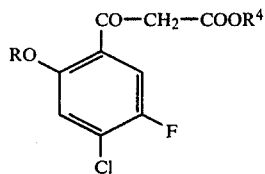

TABLE 2

| R | R⁴ | R | R⁴ | R | R⁴ |
|---|---|---|---|---|---|
| CH₃ | CH₃ | CH₃ | C₂H₅ | CH₃ | n-C₃H₇ |
| C₂H₅ | " | C₂H₅ | " | C₂H₅ | " |
| n-C₃H₇ | " | n-C₃H₇ | " | n-C₃H₇ | " |
| i-C₃H₇ | " | i-C₃H₇ | " | i-C₃H₇ | " |
| n-C₄H₉ | " | n-C₄H₉ | " | n-C₄H₉ | " |
| i-C₄H₉ | " | i-C₄H₉ | " | i-C₄H₉ | " |
| sec.-C₄H₉ | " | sec.-C₄H₉ | " | sec.-C₄H₉ | " |
| tert.-C₄H₉ | " | tert.-C₄H₉ | " | tert.-C₄H₉ | " |

The orthoformates which are to be used as the other starting materials for the process (4) according to the invention are generally defined by the formula (V). In this formula, R³ represents alkoxy. Preferably, R³ represents C₁–C₄-alkoxy.

The compounds of the formula (V) are generally known compounds of organic chemistry.

The following may be mentioned as examples of compounds of the formula (V): methyl orthoformate, ethyl orthoformate and propyl orthoformate.

The process (4) according to the invention for the preparation of the compounds of the formula (II) is preferably carried out without a diluent.

The process (4) according to the invention is in general carried out at temperatures between 80° C. and 180° C. The range between 100° C. and 160° C. is preferred. The reactions are in general carried out under normal pressure.

To carry out the process (4) according to the invention for the preparation of the compounds of the formula (II), 1 mol of the compound of the formula (IV), 1 to 2 mols preferably 1.3 to 1.7 mols of orthoformate of the formula (V) and 2 to 3 mols preferably 2 to 2.5 mols of acetic anhydride are employed. The reaction product is worked up by customary methods. The reaction product can also be employed without further purification for the next reaction.

If, for example, 2-ethoxy-4-chloro-5-fluoro-acetophenone and dimethyl carbonate are used as the starting materials for the process (6) according to the invention, the reaction can be represented by the following equation:

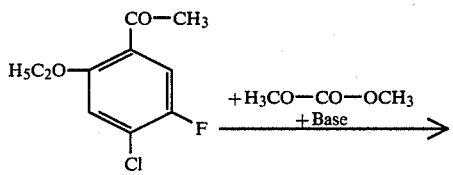

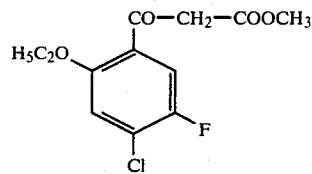

The acetophenones which are to be used as the starting materials for the process (6) according to the invention are generally defined by the formula (VI). In this formula, R preferably represents those radicals which are indicated above for formula (I).

The compounds of the formula (VI) are new. They can be prepared according to 8 (above) (see further below).

The following may be mentioned as examples of compounds of the formula (VI):
4-chloro-5-fluoro-2-methoxy-, 4-chloro-5-fluoro-2-ethoxy-, 4-chloro-5-fluoro-2-n-propoxy-, 4-chloro-5-fluoro-2-i-propoxy-, 4-chloro-5-fluoro-2-n-butoxy-, 4-chloro-5-fluoro-2-i-butoxy-, 4-chloro-5-fluoro-2-sec.-butoxy- and 4-chloro-5-fluoro-2-tert.-butoxy-acetophenone.

The dialkyl carbonates which are to be used as the other starting materials for the process (6) according to the invention are generally defined by the formula (VII). In this formula, R⁴ represents alkyl. Preferably, R⁴ represents C₁–C₄-alkyl.

The compounds of the formula (VII) are known compounds of organic chemistry.

The following may be mentioned as examples of compounds of the formula (VII): Dimethyl carbonate, diethyl carbonate and di-n-propyl carbonate.

The process (6) according to the invention for the preparation of the compounds of the formula (IV) is preferably carried out without a diluent. Preferably, it is performed in the presence of excess dialkylcarbonate of the formula (VII).

The process (6) according to the invention is carried out in the presence of strong bases. Alkali metal alcoholates, such as sodium and potassium methylate or ethylate and potassium tert.-butylate, and alkali metal hydroxides such as sodium and potassium hydroxide have proved to be particularly suitable.

For carrying out the process (6) according to the invention, 1 to 3 mols, preferably 1 to 2 mols, of a strong base and 5 to 30 mols, preferably 10 to 25 mols, of dialkyl carbonate of the formula (VII) are employed per mol of the compound of the formula (VI). Working-up is by customary methods. The reaction is in general carried out at temperatures between 0° C. and 140° C. The range between 20° C. and 120° C. is preferred. The reactions are in general carried out under normal pressure.

If, for example, 4-chloro-5-fluoro-2-hydroxyacetophenone of the formula (VIII) and methyl iodide or dimethyl sulphate are used as the starting materials for the process (8) according to the invention, the reaction can be represented by the following equation:

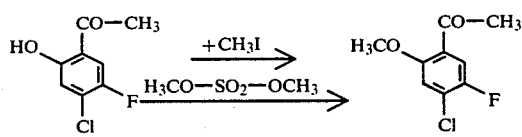

4-Chloro-5-fluoro-2-hydroxyacetophenone of the formula (VIII) which is to be used as the starting compound for the process (8) according to the invention is new. The compound can be prepared according to 10 (above) (see further below for a detailed description).

The alkyl halides or dialkyl sulphates which are to be used as the other starting materials for the process (8) according to the invention are generally defined by the formula (IX) and (X) respectively. In this formula, R preferably represents those radicals which are indicated above for formula (I).

The compounds of the formulae (IX) and (X) are generally known compounds of organic chemistry. The following may be mentioned as examples of alkyl halides of the formula (IX): Methyl chloride, methyl bromide, methyl iodide, ethyl bromide, ethyl iodide, n-propyl bromide, n-propyl iodide, i-propyl bromide, i-propyl iodide, n-butyl bromide, n-butyl iodide, i-butyl bromide, i-butyl iodide, sec.-butyl bromide, sec.-butyl iodide, tert.-butyl bromide and tert.-butyl iodide.

The following may be mentioned as examples of dialkyl sulphates of the formula (X): dimethyl sulphate, diethyl sulphate and di-n-propyl sulphate.

The process (8) according to the invention for the preparation of the compounds of the formula (VI) is preferably carried out in the presence of water or polar organic solvents. Preferably, ketones such as, for example, acetone, methyl ethyl ketone, methyl isopropyl ketone and methyl isobutyl ketone, and also nitriles such as, for example, acetonitrile and propionitrile, and moreover amides such as dimethylformamide, dimethylacetamide and N-methylpyrrolidone, and ethers such as diethyl ether, dibutyl ether, glycol dimethyl ether, diglycol dimethyl ether, tetrahydrofuran and dioxane, can be used here.

When carrying out the process (8) according to the invention, preferably strongly basic but weakly nucleophilic substances can be employed as the acid acceptors. Preferred examples are sodium hydride, potassium hydride, calcium hydride, sodium carbonate, potassium carbonate as well as calcium carbonate and diazabicyclooctane (DABCO), diazabicyclononene (DBN) and diazabicycloundecene (DBU).

In the process (8) according to the invention for the preparation of the new compounds of the formula (II) the reaction temperature can be varied within a fairly wide range. In general, temperatures between 0° C. and +100° C., preferably between 0° C. and 80° C., are used. The process (8) according to the invention is in general carried out under normal pressure.

For carrying out the process (8) according to the invention, 1 to 1.5 mols, preferably 1 to 1.2 mols, of the alkylating agent of the formula (IX) or (X) and 1 to 1.5 mols, preferably 1 to 1.2 mols, of acid acceptor are employed per mol of the compound of the formula (VIII).

The reactions are in general carried out in a suitable diluent and, if appropriate, in the presence of an acid acceptor. Working-up is by customary methods.

If, for example, 3-chloro-4-fluorophenol and acetyl chloride are used as the starting materials for the process (10) according to the invention, the reaction can be represented by the following equation:

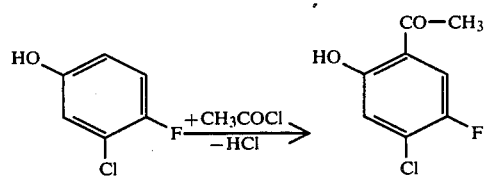

The compound 3-chloro-4-fluorophenol of the formula (XI) is used as the starting compound for the process (10).

3-Chloro-4-fluorophenol is generally known compound of organic chemistry.

The acetylating agents to be used as the other starting materials for the process (10) are generally defined by the formula (XII). In this formula, W represents halogen, such as especially fluorine, chlorine or bromine, or the radical $CH_3COO-$.

The compounds of the formula (XII) are generally known compounds of organic chemistry.

The following may be mentioned as examples of compounds of the formula (XII): Acetyl fluoride, acetyl chloride, acetyl bromide and acetic anhydride.

The acylation is carried out in the presence of known acylation catalysts. Preferred acylation catalysts which can be used for the process (10) are Friedel-Crafts catalysts. These include alumin halides, such as alumin trichloride, and boron trifluoride.

The process (10) according to the invention is preferably carried out without a diluent.

The process (10) according to the invention is in general carried out at temperatures between 0° C. and 120° C. The range between 20° C. and 100° C. is preferred. The reactions are in general carried out under normal pressure.

For carrying out the process (10) according to the invention, 1 to 2.2 mols, preferably 1 to 1.8 mols, of acetylating agent of the formula (XII) and 1 to 3.5 mols, preferably 1 to 2.8 mols, of acylation catalyst are employed per mol of 3-chloro-4-fluorophenol of the formula (XI).

Working-up is carried out in the customary manner, for example by addition of ice or ice water to the reaction mixture after the end of the reaction, and by filtering off the cooled product with suction.

The compounds of the formula (I) can be used as intermediates for the synthesis of oxoquinolinecarboxylic acid derivatives which have an outstanding bactericidal activity (compare, for example EP-OS (European Published Specification) No. 78,362). These can be prepared from the former according to the following equation:

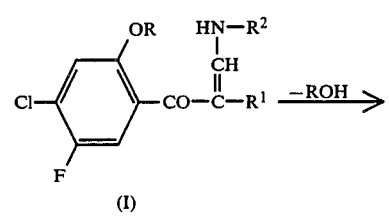

13

-continued

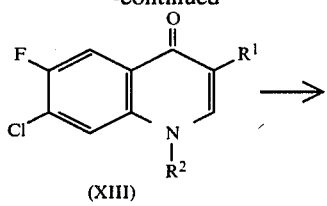
(XIII)

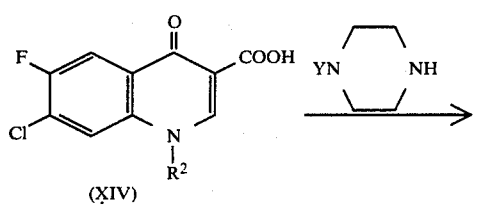
(XIV)

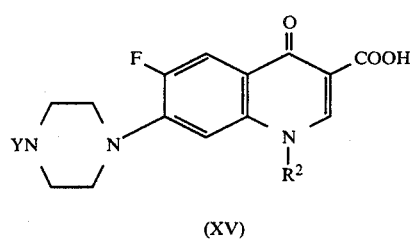
(XV)

Y = H, alkyl

The cyclization of the compounds of the formula (I) to give the known compounds of the formula (XIII) is carried out in the presence of diluents and in the presence of acid acceptors at temperatures between 60° C. and 300° C., preferably at 80° C. to 180° C.

The diluents used can be dioxane, dimethyl sulphoxide, N-methyl-pyrrolidone, sulpholan, hexamethylphosphoric acid triamide and, preferably, N,N-dimethylformamide.

The acid acceptors which can be used for this reaction are potassium tert.-butanolate, butyl-lithium, lithium phenyl, phenylmagnesium bromide, sodium methylate, sodium hydride and, particularly preferably, potassium carbonate or sodium carbonate.

When carrying out the cyclization, 1 to 1.6 mols, preferably 1 to 1.3 mols, of acid acceptor are employed per mol of the compound of the formula (I).

The reaction product is worked up in the customary manner. The further reactions of the compounds of the formula (XIII) to give the known compounds of the formulae (XIV) and (XV) have already been described (compare, for example, EP-OS (European Published Specification) No. 78,362 and EP-OS (European Published Specification) No. 113,092).

Preparation examples

EXAMPLE 1

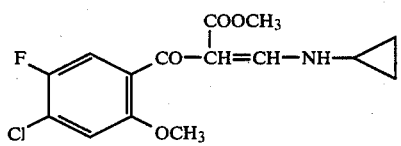

2 g (0.034 mol) of cyclopropylamine are added dropwise, with stirring, to a solution of 10.3 g (0.034 mol) of methyl 2-(4-chloro-5-fluoro-2-methoxy-benzoyl)-3-methoxy-acrylate in 40 ml of ethanol, while cooling with ice, and the mixture is stirred for a further 2 hours at 20° C. The precipitate is filtered off cold with suction and rinsed with a little ethanol.

This give 5.5 g (48.6% of theory) of methyl 2-(4-chloro-5-fluoro-2-methoxy-benzoyl)-3-cyclopropylaminoacrylate of melting point 128° C.–132° C.

Preparation of the compounds of the formula (II)

EXAMPLE (II-1)

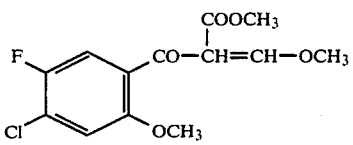

A mixture of 9.6 g (0.037 mol) of methyl 4-chloro-5-fluoro-2-methoxy-benzoylacetate, 5.5 g (0.054 mol) of trimethyl orthoformate and 8.7 g (0.087 mol) of acetic anhydride is heated for 3 hours under reflux. The volatile constituents are then distilled off under normal pressure in a water pump vacuum and finally in a high vacuum at a bath temperature of 120° C. to 130° C.

This gives 10.3 g of crude methyl 2-(4-chloro-5-fluoro-2-methoxy-benzoyl)-3-methoxy-acrylate. The product can be employed without further working-up in the next reaction stage.

Preparation of the compounds of the formula (IV)

EXAMPLE (IV-1)

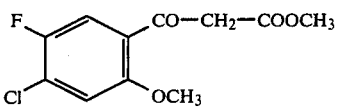

30 ml of dimethyl carbonate are distilled off from a mixture of 210 ml of diemthyl carbonate and 8.9 g (0.165 mol) of sodium methylate and a solution of 30.4 g (0.15 mol) of 4-chloro-5-fluoro-2-methoxy-acetophenone in 75 ml of dimethyl carbonate is then added dropwise to the reaction mixture at the boil in the course of 3 hours. During this period, the methanol formed in the reaction is distilled off through a column. Boiling under reflux is continued for a further 3 hours after the addition, and the solvent is then distilled off in vacuo. The residue is dissolved in 500 ml of water, concentrated hydrochloric acid is added at 10° C. until a pH of 6 is reached, and the mixture is then extracted with twice 200 ml of methylene chloride. The organic phase is dried over sodium sulphate, evaporated in vacuo and then partially distilled in a high vacuum at 120° C. 2.4 g of the 4-chloro-5-fluoro-2-methoxy-acetophenone are recovered in this way.

As the residue, 32 g (89% of theory) of methyl 4-chloro-5-fluoro-2-methoxy-benzoylacetate remain in the form of a light brown powder of melting point 61° C.

Preparation of the compounds of the formula (VI)

EXAMPLE (VI-1)

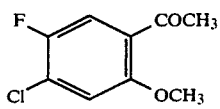

A mixture of 7.5 g (0.04 mol) of 4-chloro-5-fluoro-2-hydroxy-acetophenone, 8.3 g (0.06 mol) of potassium carbonate, 50 ml of acetonitrile and 6.3 g (0.044 mol) of methyl iodide is stirred for 7 hours at 55° C. The reaction mixture is then filtered and the filtrate is evaporated in vacuo. The residue is triturated with 50 ml of water and the solid is filtered off with suction.

This gives 7.4 g (92% of theory) of 4-chloro-5-fluoro-2-methoxy-acetophenone in the form of a beige powder of melting point 80° C.

Preparation of the compound of the formula (VIII)

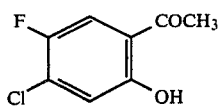

9.5 g (0.12 mol) of acetyl chloride are added dropwise at 20° to 30° C. to a mixture of 11.8 g (0.08 mol) of 3-chloro-4-fluorophenol and 26.8 g (0.2 mol) of aluminum chloride. The mixture is stirred for 1 hour at 95° to 100° C. and then, while still hot, poured onto a mixture of 300 g of ice and 100 ml of water. After 30 minutes, the precipitated product is filtered off with suction and thoroughly washed with water.

This gives 12.9 g (86% of theory) of 4-chloro-5-fluoro-2-hydroxy-acetophenone in the form of a beige powder of melting point 72° C.

Preparation of the compounds of the formula (XIII)

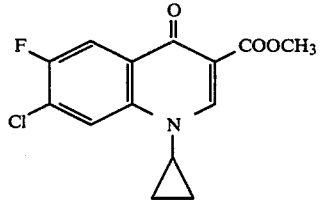

A suspension of 5.2 g (0.016 mol) of methyl 2-(4-chloro-5-fluoro-2-methoxy-benzoyl)-3-cyclopropylaminoacrylate (Example 1), 2.6 g (0.019 mol) of potassium carbonate and 25 ml of dimethylformamide is heated for 2 hours to about 150° C. The reaction mixture is then poured onto ice, and the precipitate is filtered off with suction and rinsed with water. After drying in a vacuum drying cabinet at 100° C., 3.6 g of crude product are obtained.

Recrystallization from ethanol gives 3.1 g (66% of theory) of methyl 7-chloro-1-cyclopropyl-6-fluoro-1,4-dihydro-4-oxo-quinolinecarboxylate of melting point 244° C.-245° C.

It will be understood that the specification and examples are illustrative but not limitative of the present invention and that other embodiments within the spirit and scope of the invention will suggest themselves to those skilled in the art.

What is claimed is:

1. An aminoacrylic acid derivative of the formula

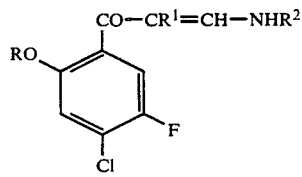

in which
R is alkyl,
$R^1$ is alkoxycarbonyl, and
$R^2$ is $C_3$-$C_6$-cycloalkyl.

2. A compound according to claim 1, in which
R is $C_1$-$C_4$-alkyl, and
R' is $C_1$-$C_4$-alkoxycarbonyl.

3. A compound according to claim 1, in which
R is methyl, ethyl or propyl,
R' is methoxycarbonyl, ethoxycarbonyl or n-propoxycarbonyl, and
$R^2$ is cyclopropyl.

4. A compound of the formula

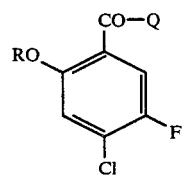

in which
Q is —$CR^1$=$CHR^3$ or —$CH_2COOR^4$,
R is alkyl,
$R^1$ is alkoxycarbonyl,
$R^3$ is alkoxy, and
$R^4$ is alkyl.

5. An acrylic acid derivative according to claim 4 of the formula

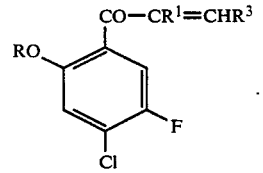

6. A 2-alkoxy-4-chloro-5-fluoro-benzoylacetate according to claim 4 of the formula

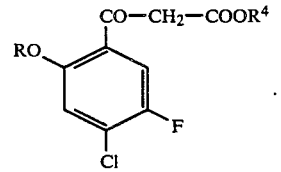

* * * * *